United States Patent
Hinnrichs et al.

(10) Patent No.: US 6,680,778 B2
(45) Date of Patent: Jan. 20, 2004

(54) GAS LEAK DETECTOR

(76) Inventors: Michele Hinnrichs, 1001 Croft La., Solvang, CA (US) 93463; Robert Hinnrichs, 1001 Croft La., Solvang, CA (US) 93463

( * ) Notice: Subject to any disclaimer, the term of this patent is extended or adjusted under 35 U.S.C. 154(b) by 93 days.

(21) Appl. No.: 10/007,080

(22) Filed: Nov. 8, 2001

(65) Prior Publication Data

US 2003/0086091 A1 May 8, 2003

(51) Int. Cl.⁷ .............................. G01N 21/00
(52) U.S. Cl. ................ 356/437; 356/310; 356/330
(58) Field of Search ................. 356/434, 437, 356/436, 432, 433; 250/338.5, 339.13

(56) References Cited

U.S. PATENT DOCUMENTS

| | | | | |
|---|---|---|---|---|
| 4,147,431 A | * | 4/1979 | Mann | 356/72 |
| 5,015,099 A | * | 5/1991 | Nagai et al. | 356/437 |
| 5,479,258 A | * | 12/1995 | Hinnrichs et al. | 356/326 |
| 5,867,264 A | * | 2/1999 | Hinnrichs | 356/310 |
| 5,892,586 A | * | 4/1999 | Thony et al. | 356/437 |

* cited by examiner

Primary Examiner—Hoa Q. Pham
(74) Attorney, Agent, or Firm—Michael G. Petit

(57) ABSTRACT

A remote sensing method for detecting and analyzing gases, vapors and flame plumes using an imaging spectrometer. The spectrometric instrument uses Image Multispectral Sensing (IMSS) technology, enhanced by advanced imaging processing techniques and micro-miniature circuitry. These enhancements provide a portable instrument with the capability to remotely detect and image gases, including gas leaks. The technology also provides an analysis of the gas including chemical species and concentrations. The instrument can also remotely detect, image and analyze flames and plumes in the same manner, providing an analysis of the chemical species and concentrations in the flame. Advanced image processing techniques are used to provide gas and plume images and analysis to the operator. These processing algorithms are implemented in micro-miniature circuits such as digital signal processors (DSP's) and field programmable gate arrays (FPGA's) to provide a field portable instrument.

5 Claims, 4 Drawing Sheets

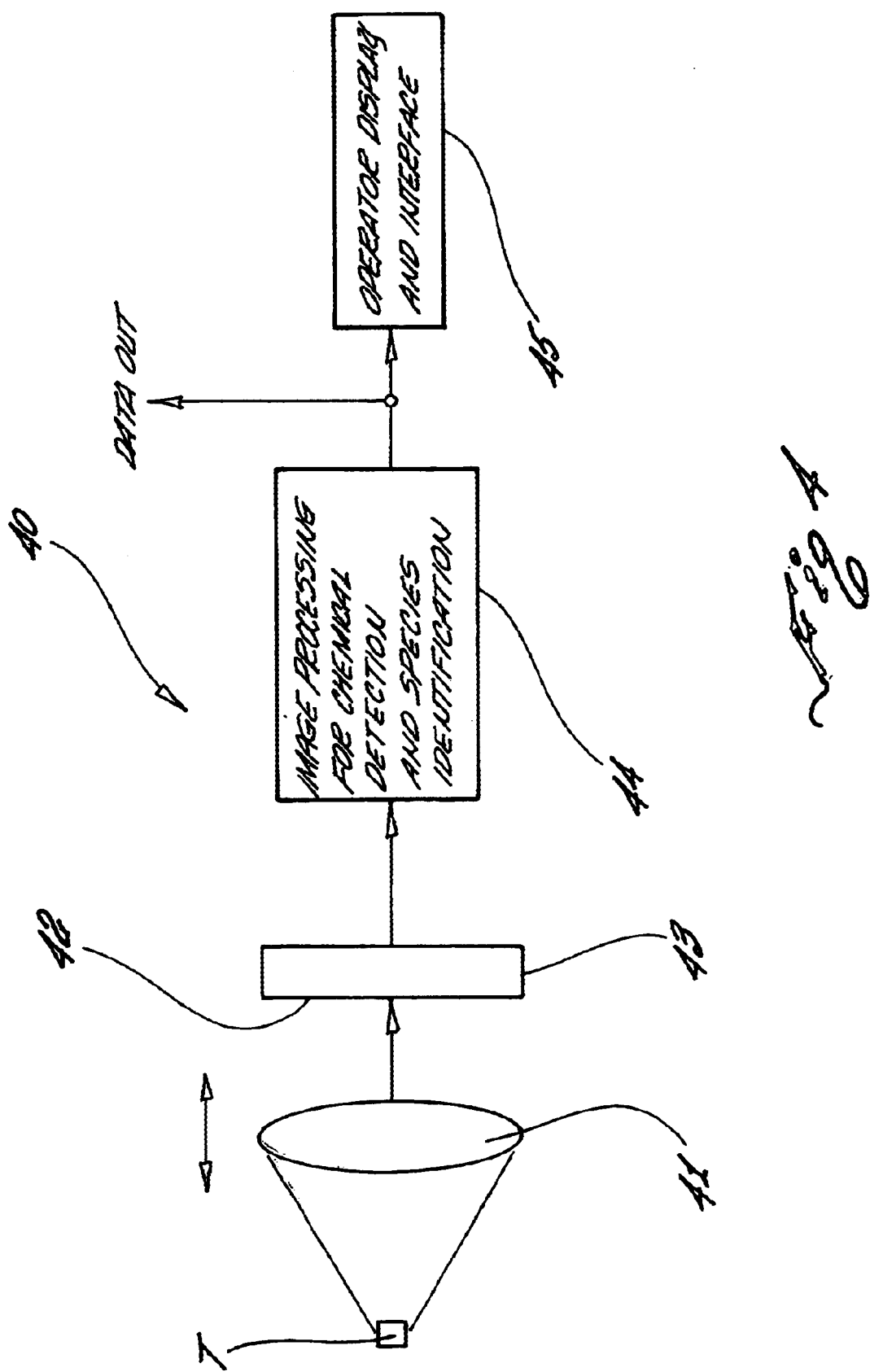

GAS LEAK DETECTOR

BACKGROUND OF THE INVENTION

1. Field of the Invention

This invention is an imaging spectrometer useful for measuring the spectral composition of gases emanating from a gas leak at a remote location, and, more particularly, provides a method and apparatus for locating gas leaks.

2. Prior Art

Gas producers and distributors lose millions of dollars annually due to gas leakage from a distribution line, processing or containment facility. A portable instrument with the capability to remotely detect and image gases, including gas leaks, is needed. Such a device and method for finding and identifying gas leaks should preferably further provide an analysis of the gas including chemical species and concentrations.

Spectrophotometers (color meters) are widely used in the area of target recognition. The principle underlying the use of spectrophotometers in target recognition is that different targets reflect, emit or absorb light differently. Alternatively, different targets represent independent light sources, the light emanating from each target having an observable spectra which is an identifiable inherent characteristic of that target which may be used for target identification.

Image multispectral sensing (IMSS) records the spectrum of individual luminous objects (targets) within an image or scene. IMSS is capable of simultaneously recording the spectrum of light emerging from many different discrete light sources contained within a single field of view. U.S. Pat. No. 5,479,258 to Hinnrichs et al., the contents of which is incorporated herein by reference thereto, discloses an image multispectral sensing device, which provides good spectral resolution for images comprising luminous point objects which have good contrast ratios with respect to the background. The ability of IMSS spectrometers to distinguish between an object and a background may be extended to the detection of a non-homogeneous distribution of gases in a volume of gas. There is a need for an IMSS apparatus which is adapted to be portable and operable for detecting gas leaks at remote locations.

SUMMARY OF THE INVENTION

It is an object of this invention to provide a spectrometric apparatus for measuring the spectral composition of infrared, visible or ultraviolet light emanating from a volume of gas located at a distance from the apparatus.

It is yet another object of this invention to provide a imaging spectrometer apparatus which can determine the spectral composition of light emanating from different portions of a large volume of gas comprising a remote field of view.

It is another object of this invention to provide a imaging spectrometer apparatus useful for comparing the spectral composition of light (color signature) emanating from a remote luminous volume of gas within a field of view with the color signature of previously identified luminous gases or mixtures of gases.

It is a particular object of the invention to provide a IMSS apparatus operable for performing the above objects and which can detect the presence of a gas leak from a gas containment device, or components is a processing or distribution system.

These and other aspects of the invention will soon become apparent in view of the drawings and description of the preferred embodiments.

BRIEF DESCRIPTION OF THE DRAWINGS

FIG. 4 is a schematic diagram of a gas detection instrument in accordance with the present invention, adapted for detecting gas leaks.

DESCRIPTION OF THE PREFERRED EMBODIMENT

Figure 3:
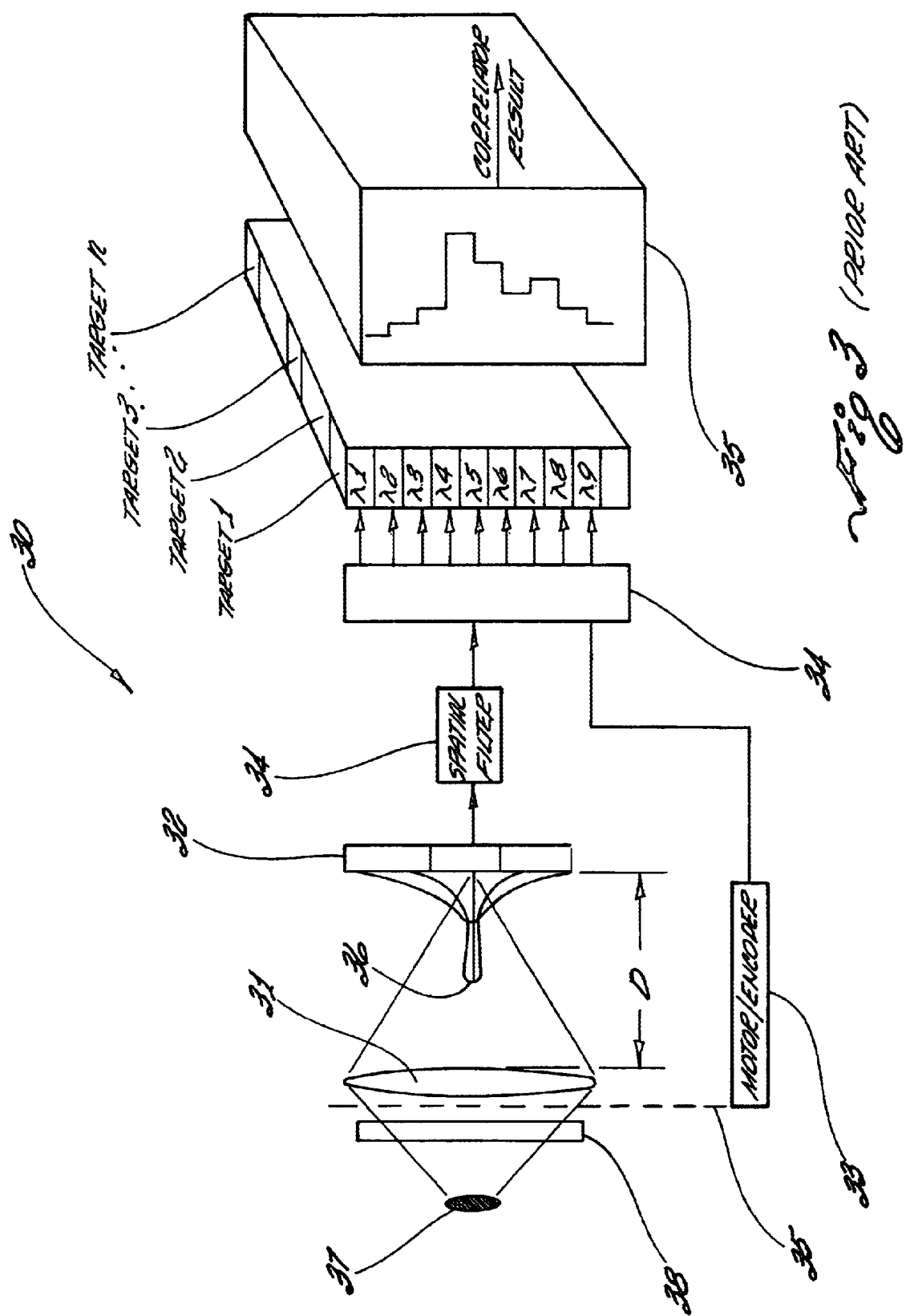
FIG. 3 is a schematic diagram of an IMSS spectrophotometer showing the optical relationship of the addressable transmissive spatial mask (35) with respect to the input optics for controlling transmission of the image projected thereon to the diffractive lens (31) for dispersion and to the photodetector (32) for spectral detection.

The present invention provides an apparatus and method for identifying the presence of a gas leak at a location remote from the apparatus. The apparatus is a IMSS spectrometer incorporating an addressable spacial mask which permits the spectral composition of a single pixel to be determined even when the image comprises more than one independent source of light. A prior art IMSS system is shown in FIG. 3. The apparatus 30 comprises a diffractive lens 31 having an optical axis, a photodetector 32 having a planar photosensitive surface orthogonal to the optical axis and intersecting the optical axis at a distance f from the diffractive lens, a stepping motor 33, which may include an optional shaft position encoder, adapted to change D a known amount in response to a control signal, a programmable signal processor 34 which includes programmable computer means adapted to provide a control signal to the stepping motor 33 for changing D and provide control signals to the gates and identify and synchronously record the output signal of the pixel in optical communication with the gate. The signal processor is adapted to receive and organize the output signals from each pixel within the photodetector into a sequence of frames, each frame in the sequence containing the signal output of each pixel at a focal plane f corresponding to an input of the position encoder 33 identifying a focal plane, process the frames to spectrally filter the spectral data and present the processed spectral data to a spectral correlator 35 for comparison, identification storage, or for future reference purposes. Light 36 emanating from a remote target 37 within a field of view is collimated by input optics 38 which directs the light 36 comprising an image of the field of view to impinge upon a diffractive lens 31. The light 36 is focused by the diffractive lens 31 onto the photodetector 32. The distance f between the photodetector array 32 and the diffractive lens 31 is controlled by mounting one of the components 31 or 32 on translating means 33 such as a stepper motor, a piezoelectric translation device or other such translating device capable of varying D to traverse the range of focal lengths encompassing the spectral components of the light 36. The distance D, which is the instantaneous distance between the diffractive lens 31 and the photodetector 32 along the optic axis, is determined by a stepping motor 33, which is controlled by the signal processor 34. The signal processor records the signal output of each pixel (not shown in FIG. 3) in the photodetector 32. Thus, for every value of D, only luminous objects comprising the image having a spectral component is in sharp focus at the plane of the photodetector 32 will be recorded within the frame corresponding to the focal plane for the spectral component. If the image includes multiple light sources or targets, the intensity of the spectral component of light emanating from targets 1 through n in the image are recorded within a frame for each value of D as shown. The record of the signal output of each pixel within the photodetector corresponding to a particular focal distance (wavelength $\lambda$) comprises a single frame. In FIG. 3, only a single target 37 is shown. The relative intensity and wavelength of the spectral components $\lambda_1-\lambda_9$ of the light 36 emanating from the target 37, may be compared with spectral data stored within the memory of a spectral correlator 35. The correlator 35 provides a means for storing and comparing spectral data.

Figure 1:
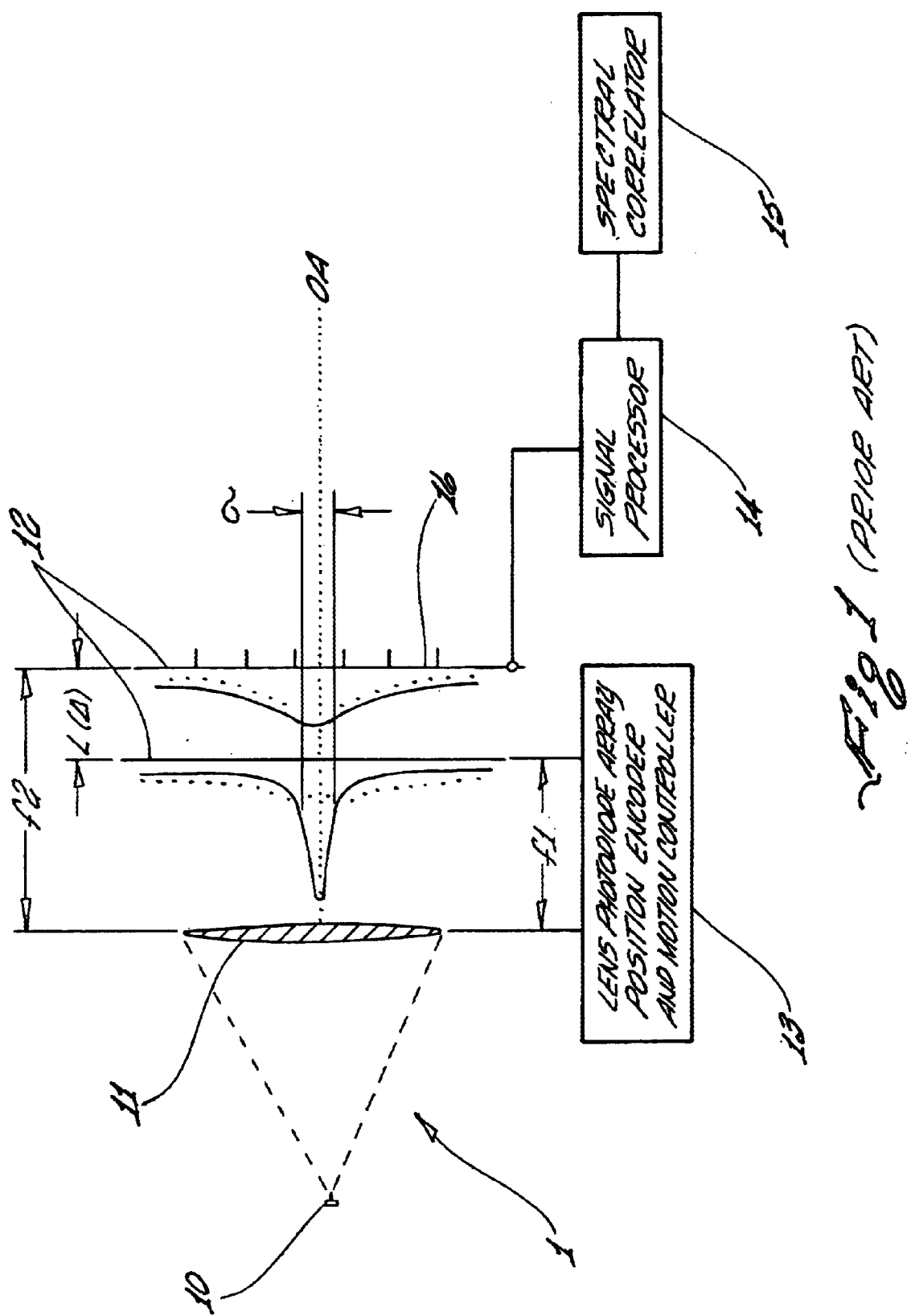
FIG. 1 is a schematic diagram showing red and blue spectral components of dispersed polychromatic light emerging from a diffractive lens in sharp focus at different focal planes along the optic axis.
Figure 2:
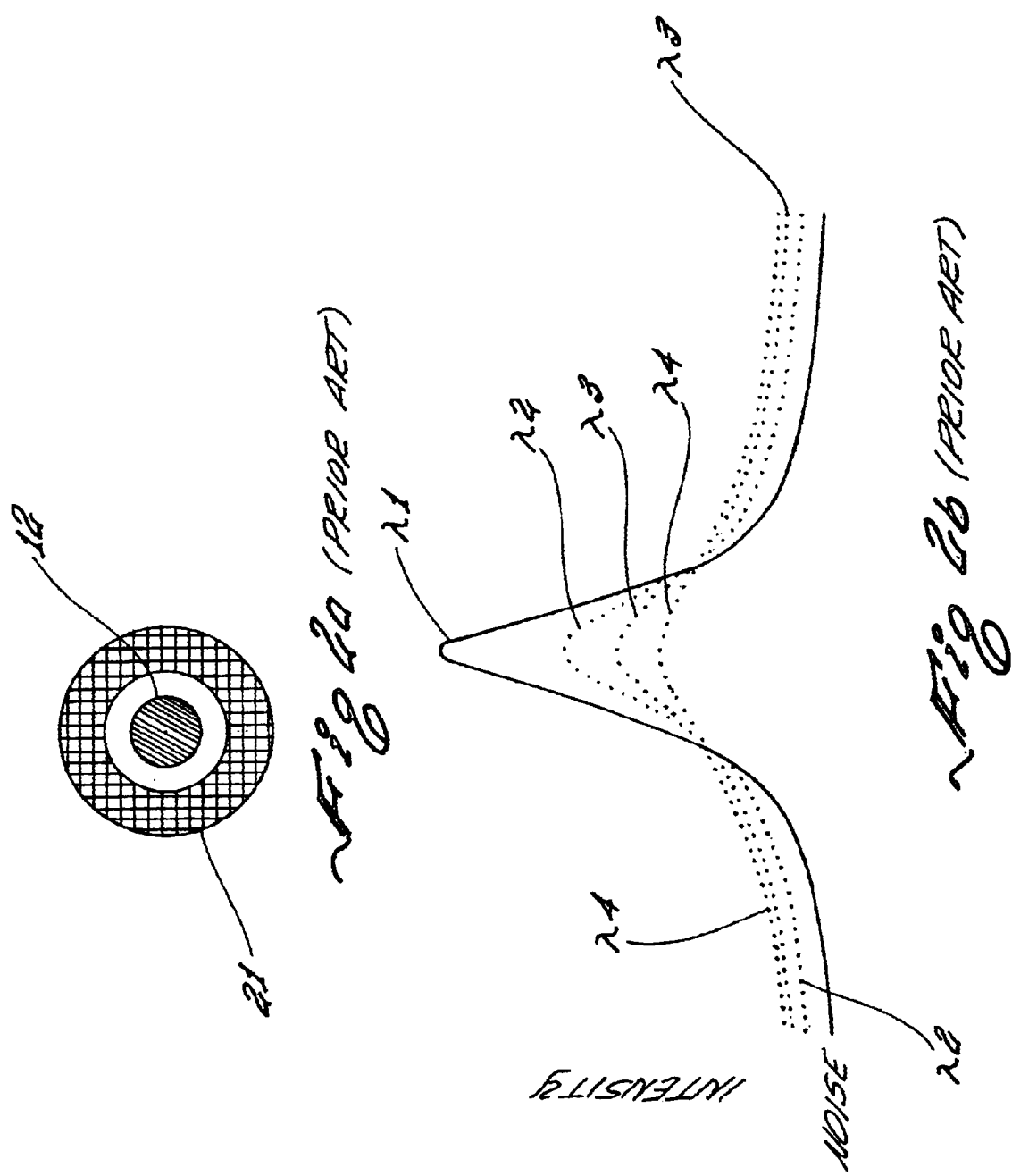
FIGS. 2(a) and 2(b) show the intensity distribution of dispersed spectral components of light from a single point source illuminating a photosensitive surface and show the relative intensity of the in-focus spectral component having a wavelength $\lambda_1$ with respect to the superimposed intensity of out-of-focus spectral components of the dispersed light at the focal plane of $\lambda_1$ and generally illustrating the relationship between spectral resolution in of the in-focus image and the out-of-focus background.

As stated earlier, the signal output of each pixel within the photodetector array 12 is electronically scanned into a signal processor 34. The signal processor compares the signal output of each pixel with the signal output of pixels immediately adjacent thereto. If the signal output of the adjacent pixels is uniformly lower than the output of the pixel being processed, the uniform output signal may be attributed to noise and subtracted from the measured signal output of the pixel to provide a measure of the intensity of the in-focus spectral component. The process is repeated for each pixel having a signal output greater than a threshold value and the electronically filtered spectral intensity data is stored in a frame. The procedure is repeated at incremental focal planes until frames encompassing the spectral range of interest are recorded. For example, with reference to FIG. 1, when the photodetector 12 is at the position of $f_r$, only the red spectral component will be in focus at pixel 16 and remain in the frame corresponding to $f_r$ after signal processing at the position $f_b$ only the blue spectral component will pass through the signal processing filter and appear as the only signal output in the frame corresponding to $f_b$.

The change in distance between the diffractive lens and the photodetector required for IMSS must be sufficient to span the range of focal lengths for the spectral components of interest in the target-derived light. For example, a piezoelectric driven movable element may be used to mount the diffractive lens. Focal length scans of 160 millimeters per second are practical with this approach. A stepper motor or a pneumatic/hydraulic translational device can also be employed for changing the distance f between the diffractive element and the photodetector when either of the components are moved thereby thereon.

The defocused spectral components of light comprising the spectra of nearby independent sources of light within the image will also impose noise upon a pixel's output signal. If the out-of-focus spectral component from an adjacent target is very intense, it can dramatically and asymmetrically effect the signal output of the pixel receiving the in-focus spectral component of the less luminous light source. The apparatus employs an addressable spatial mask, shown in phantom at 35 in FIG. 3, disposed between the input optics 38 and the diffractive lens 11 to shadow one of a plurality of adjacent light sources in an image to reduce interspectral noise at the photodetector. The mask has an image receiving surface which consists of a planar array of discrete, addressable, independently controllable optical gates disposed to receive an image projected thereon by the input optics. The function of the mask is to select only a pixel-sized portion of the image incident thereon and sequentially direct the gated pixel-sized portion of the image to be dispersed by the diffractive lens. The diffractive lens focuses the spectral components to illuminate the photodetector. Light from other portions of the image are blocked out while the signal output of the pixel receiving the gated light is synchronously recorded. Each of the plurality of switchable gates forming the image-receiving surface of the mask are sequentially "switched" in response to a control signal from the signal processor and will direct only the portion of the image incident thereon to the diffractive lens in synchronization with the electronic readout of the pixel upon which the gated light is focused. In this manner each spectral component comprising the image is sequentially mapped onto the photodetector surface a "gate-full" at a time in synchronization with the sequential output sampling of the gate-sized pixel in the photodetector upon which the gated light is focused. Out-of-focus light from other spatially separated portions of the image is blocked out.

With reference now to FIG. 4, a preferred embodiment 40 of the present invention is illustrated in diagrammatic view. A diffractive optical element 41 is used to focus an image of the target chemical under analysis on a photosensitive surface 42 of a detector 43 (such as a focal plane array (FPA)). An image of the scene under view is formed on the detector 43. As discussed above, the IMSS diffractive optical element 41 focuses different wavelengths of light at different distances or focal lengths. The distance between the diffractive optical element 41 and the detector 43 is changed to form a series of very narrowband spectral images. The images are stored in the image processing electronics 44. The image processing electronics 44 uses these spectral images to detect and image the target chemical by techniques such as, for example, by comparing the image at the absorption band of the target chemical to images outside the absorption band, using motion detection algorithms, and applying techniques such as principle components analysis. A raw image and a processed image of the target chemical can be provided to the operator via operator display 45.

The instrument 40 can also identify an unknown chemical. The spectrum of an unknown target chemical obtained by the instrument is compared with a spectral database of chemical spectra stored in the image processing electronics to identify the chemical species of the target chemical. Concentrations of the target chemical are obtained by determining the absorption (or emission in the case of a flame or plume) of the target chemical at its absorption wavelength (or emission wavelength) compared to images outside the absorption or emission region.

In view of the foregoing, and in light of the objectives of the invention, it will be apparent to those skilled in the art that the subject matter of this invention is capable of variation in its detail, and we do not therefore desire to be limited to the specific embodiments of the apparatus selected for purposes of explanation of the invention. For example, it is possible to employ a diffractive lens for the chromatic dispersion of light wherein the particular wavelength of light in focus at a particular point in space depends on the electromechanical forces applied to the lens. A diffractive optical element can be made using polymer or spatial light modulators which change the characteristics of the lens such that the chromatic focal length of the lens can be adjusted by application of an appropriate electrical signal to the lens. In such a case there is no need to move the diffractive lens relative to either the spatial mask or the photodetector array to perform Image Multispectral Sensing. The foregoing has been merely a description of one embodiment of the imaging spectrophotometer that may be used to detect gas leaks. The scope of the invention can be determined by reference to the claims appended hereto.

What we claim is:

1. A method for detecting the presence of a particular gas in a volume of gas comprising the steps of:

(a) presenting an image multispectral sensing apparatus operable for measuring the spectral composition of light emanating from a remote volume of gas, the apparatus having a light input aperture; then (b) gathering light from said volume of gas and focusing an image containing said light on said input aperture; then (c) measuring the spectral composition of light from different parts of the image to determine the spectral distribution, the spectral distribution indicating the presence of a gas leak.

2. The method of claim 1 wherein said image multispectral sensing apparatus comprises:

(a) an input optical element adapted to receive and transmit said light emanating from a remote volume of gas; and (b) a diffractive optical element having an optical axis and disposed to receive said light transmitted by said input optical element and adapted to disperse spectral components of said light into a volume having an area A and a length L, said area A defining a pixel footprint; and (c) a photodetector array comprising a plurality of pixels, said photodetector array having an area substantially equal to said pixel footprint, said photodetector array being disposed to receive dispersed light from said diffractive optical element; and (d) means for measuring said controllable portion of said light that is focused upon said photodetector array, said measured controllable portion comprising an image; and (e) means for changing the distance between said diffractive optical element and said photodetector array in the direction of L.

3. The method in accordance with claim 2 wherein said image multispectral sensing apparatus further comprises:

(a) an addressable spatial mask disposed between said input optical element and said diffractive optical element comprising a sheet having a planar array of discrete addressable switchable apertures disposed thereon, said apertures being independently operable for directing a controllable portion of said light incident thereon to said diffractive optical element in response to a control signal; and (b) means for controlling the direction of said light incident upon each of said plurality of apertures of said addressable spatial mask to impinge upon said diffractive optical element.

4. The method of claim 2 wherein said image multispectral sensing apparatus further comprises computer means operable for enhancing said image.

5. The method of claim 3 wherein said image multispectral sensing apparatus further comprises computer means operable for enhancing said image.

* * * * *